United States Patent
Renzin et al.

(10) Patent No.: US 8,247,637 B2
(45) Date of Patent: Aug. 21, 2012

(54) MINI PAD FOR REDUCING INFLAMMATION OF THE VULVA AND METHOD OF MAKING THE SAME

(75) Inventors: Stephen M. Renzin, Larchmont, NY (US); William Schmitt, Branford, CT (US)

(73) Assignee: Femaceuticals, LLC, Larchmont, NY (US)

( * ) Notice: Subject to any disclaimer, the term of this patent is extended or adjusted under 35 U.S.C. 154(b) by 934 days.

(21) Appl. No.: 11/572,462

(22) PCT Filed: Jul. 20, 2005

(86) PCT No.: PCT/US2005/025672
§ 371 (c)(1),
(2), (4) Date: Jan. 22, 2007

(87) PCT Pub. No.: WO2006/014693
PCT Pub. Date: Feb. 9, 2006

(65) Prior Publication Data
US 2008/0033384 A1 Feb. 7, 2008

Related U.S. Application Data

(60) Provisional application No. 60/590,326, filed on Jul. 23, 2004.

(51) Int. Cl.
*A61F 13/20* (2006.01)
(52) U.S. Cl. ... 604/361; 604/358; 604/367; 604/385.23; 604/386; 604/387; 604/365; 604/374; 604/375; 604/384; 604/385.21; 604/381; 27/19; 27/21.1; 27/1; 27/35; 5/484; 5/487
(58) Field of Classification Search .................. 604/358, 604/361, 367
See application file for complete search history.

(56) References Cited

U.S. PATENT DOCUMENTS

| | | | | |
|---|---|---|---|---|
| 3,340,153 A | * | 9/1967 | Werner | 514/775 |
| 3,483,008 A | * | 12/1969 | Herr | 106/156.21 |
| 3,959,491 A | * | 5/1976 | Young et al. | 514/775 |
| 4,129,645 A | * | 12/1978 | Barnett et al. | 424/60 |
| 4,240,436 A | | 12/1980 | Singleton | 128/403 |
| 4,540,567 A | | 9/1985 | Oneto et al. | 424/45 |
| 4,556,146 A | * | 12/1985 | Swanson et al. | 206/440 |
| 4,743,245 A | | 5/1988 | Lassen et al. | 604/385 |
| 4,780,117 A | | 10/1988 | Lahey et al. | 62/4 |
| 4,842,884 A | * | 6/1989 | Bookwalter et al. | 426/585 |
| 4,986,076 A | | 1/1991 | Kirk et al. | 62/4 |
| 5,167,655 A | | 12/1992 | McCoy | |
| 5,428,016 A | | 6/1995 | Tomita et al. | 514/15 |

(Continued)

FOREIGN PATENT DOCUMENTS
DE 665384 9/1938
(Continued)

*Primary Examiner* — Tatyana Zalukaeva
*Assistant Examiner* — Ilya Treyger
(74) *Attorney, Agent, or Firm* — William W. Jones

(57) ABSTRACT

A mini pad is provided with a chilled skim milk additive which is useful for reducing vulvar inflammation and lowering the acidity of a female's vulva which result from vaginal secretions which leak onto the tissue of the vulva. The mini pad can be provided with a self-contained cooling component which can be frozen or, when compressed and ruptured, will lower the temperature of the mini pad to provide the soothing cold. The skim milk can be incorporated into the mini pad in several different ways. The mini pad is useful for soothing and healing vulvar irritation, and it is mobile and can be easily used during normal daily activities without any problems whatsoever.

1 Claim, 2 Drawing Sheets

U.S. PATENT DOCUMENTS

| | | | |
|---|---|---|---|
| 5,645,830 A | 7/1997 | Reid et al. | 424/93.45 |
| 5,707,645 A | 1/1998 | Wierson | 424/436 |
| 6,004,551 A | 12/1999 | Reid et al. | 424/93.45 |
| 6,233,945 B1 | 5/2001 | Kohout | 62/4 |
| 6,393,843 B2 | 5/2002 | Kohout | 62/4 |
| 6,468,526 B2 | 10/2002 | Chrisope | 424/93 |
| 6,761,885 B1 * | 7/2004 | Håkansson et al. | 424/93.45 |
| 6,972,010 B2 * | 12/2005 | Pesce et al. | 604/289 |
| 2003/0036740 A1 | 2/2003 | Hammonds et al. | 604/385.04 |

FOREIGN PATENT DOCUMENTS

| | | | |
|---|---|---|---|
| DE | 710483 | | 9/1941 |
| JP | 61-172126 | | 10/1986 |
| JP | 9-291024 | | 11/1997 |
| JP | 2001-299801 | | 10/2001 |
| RU | 2183935 | * | 6/2002 |
| WO | WO 9917813 | | 4/1999 |
| WO | WO 2004032985 | | 5/2004 |

* cited by examiner

MINI PAD FOR REDUCING INFLAMMATION OF THE VULVA AND METHOD OF MAKING THE SAME

Applicant hereby claims priority benefits of PCT Patent Application No. PCT/US05/25672 filed Jul. 20, 2005, which claims the benefit of U.S. Provisional Patent Application No. 60/590,326 filed Jul. 23, 2004, the disclosures of which are herein incorporated by reference.

TECHNICAL FIELD

This invention relates to a mini pad for reducing vulvar inflammation in females, and to a method for making the same. More particularly, this invention relates to a mini pad of the character described which is tidy, convenient to use, and can be worn during most conventional daily activities in order to relieve or prevent vulvar irritations. Vulvar irritations are often caused by vaginal secretions deposited on the vulva, or by direct irritation of the tissue by such things as tight clothing, excessive exposure to persistent moisture or perspiration, or mild trauma from sexual relations. As a result, the delicate vulva tissue becomes inflamed and irritated. Increased acidity of the tissue in this area is one of the factors causing annoying symptoms.

BACKGROUND ART

Vulvar inflammation and irritation is a major problem with most females beginning essentially at puberty. As noted above, this problem can be the result of vaginal secretions which are deposited on the vulva. These secretions inflame vulvar tissue and result in uncomfortable irritation and itching of the vulva tissues. Increased acidity of the irritated skin is the major reason for the vulvar discomfort.

This problem has been addressed with topical steroid creams which are manually applied to the affected tissue by the user. The use of such topical steroid creams has been effective in dealing with the problem, but they are messy to use, and can undesirably stain undergarments, and with long term use they can cause skin damage as well. Females who endure this problem have also been advised to, in the privacy of their homes, saturate a towel with water, and place the saturated towel in a freezer so as to freeze the water and then add skim milk to the top of the frozen towel. The frozen towel is then applied to the irritated area so as to soothe and reduce the irritation. This approach has also proven to be successful, but it cannot be used by women except in the privacy of their homes. Thus, a woman enduring this irritation problem cannot use the frozen towel remedy during normal daily activities. It would be desirable to provide a readily usable solution to the problem of vulvar irritation which would reduce the acidity of the tissues in question, while soothing the irritation encountered. The product incorporating the solution to the problem should be readily usable during daily activity of the subject, be non-messy, and be relatively inexpensive and simple to produce, without requiring FDA approval.

DISCLOSURE OF THE INVENTION

This invention is directed to a modified mini pad which incorporates a milk ingredient that, when applied to the irritated tissue will lower the acidity of the tissue and, because of other materials such as proteins in the milk, soothe the inflamed area. The mini pad can contain an endothermic refrigerant cooling component that can be made cold by crushing, or it can contain a gel cooling component that can be cooled by being placed in a refrigerator or freezer. The mini pad has a relatively conventional configuration with a slight bulge in the middle so as to obtain intimate contact with the individual's skin. The milk component can be incorporated into the pad in a number of different ways. For example it has been found that slurries of nonfat dry milk in water can be formed, sprayed onto the pad, dried and then are suitable for use. Alternatively, slurries of nonfat dry milk and a meltable anhydrous water-soluble carrier such as polyethylene glycol can be formed. Alternatively, a slurry of nonfat dry milk and a non-water-soluble carrier such as mineral oil and wax can be formed. A slurry of nonfat dry milk and an aqueous solution of thickeners and polymers can be formed. The aforesaid dry milk can be substituted with non-dry milk, and whole milk, both liquid and dry can be used in place of the nonfat milk component. Nonfat dry milk is preferred. When a liquid milk product, either whole or nonfat, is used, the milk product would be dried after being applied to the pad. Any combination of the dry or liquid milk components, either nonfat, or whole milk, can be used in producing the pad.

When using a wet slurry production protocol, the pad should be provided with a non-woven outer cover onto which the milk component is coated. The outer cover can be made from polyethylene, polypropylene, and/or polyamides, such as nylon, PET, rayon, cellulose, cotton, viscose, acrylics and fibers from wood pulp. The non-woven covers can be made by spin bonding, melt blowing, needle punching, resin bonding, air laying, hydro entangling, caustic entangling, wet laying, spin lacing and carding, depending on which of the materials are being used to make the cover. The milk component can be applied to the pad cover before assembly of the pad, i.e., before the pad is placed in the pad cover, or after assembly of the pad. The milk coating can be applied to the pad cover by a doctor blade, by rollers, or by spraying. When an aqueous solution of the milk component is used, the coated pad or pad cover must be dried before the pad is ready for use. Drying can be accomplished either by forced air drying or by direct application of heat through forced hot air, heated rollers, bars or plates. The pad assembly can include the absorbent filler pad, and/or polymers, such as high molecular weight acrylics, commonly referred to as "super slurpers", to hold moisture and may also include a pouch containing a freezable liquid which can be frozen and slipped into the pad.

The finished pad assembly is used in the following manner. When the milk is applied to an outer non-woven pad cover, the dried milk constituent will be in intimate contact with the subject's skin. It should be realized that when the milk slurry is dried on the pad's outer surface, the concentration of milk on the pad will be more highly concentrated than if moist milk were to be used without drying the milk coating. Thus, the natural moisture of the skin will dissolve or release the fat-free or whole milk to the skin. This result can be accelerated by having a semi-permeable sheet material between the outer non-woven cover and the interior of the pad. The cover serves to prevent transepidermal moisture from bypassing the dried milk, and ensures that the transepidermal moisture will solubilize the dried milk solids into a milk solution or mixture. The use of such a sheet material will increase the concentration of transepidermal water vapor such that the water vapor will enhance release of milk to the vaginal area.

In the case of application of the milk constituent to the assembled pad, the concentration of milk on the exterior and interior of the pad will depend on how it is applied, i.e., by cylinder or by spray. Use of a cylinder which directly contacts the non-woven sheet material to coat the sheet material will result in a greater concentration of milk on the sheet material due to the direct contact that occurs between the cylinder and the sheet material. The concentration of milk in the pad will be able to be thus controlled along with the formulation type, i.e., either hydrophobic or hydrophilic, to affect both instant and/or sustained release of milk from the pad to the vaginal area. A hydrophilic formulation will more readily result in release of the milk for the pad assembly because of the transepidermal moisture. If the formulation is hydrophilic, milk release can be slowed by increasing the molecular weight of the incorporated material. Polyethylene glycol is one example of such a material. If the material is hydrophobic, materials such as silicone can be used to retard the release of the milk constituent. Thus, the pad assembly can be customized to a certain degree regarding the rate of release of the milk constituent. A preferred embodiment of the pad assembly could employ an accelerated release of the milk constituent initially, followed by a slower, more sustained release of the milk constituent. The use of a polyethylene glycol matrix which includes different molecular weight fractions would achieve this desired result.

The pad assembly can be impregnated with the milk component in a number of other ways which do not involve the formation of a milk slurry per se. One way would be to spray or coat the pad material with water, or an aqueous slurry of a sticky substance, and then sprinkle dry milk on the wet pad material. The sprinkled pad material would then be dried. One could also spray or coat the pad material with a concentrated solution or slurry or a non-concentrated solution of wet milk and then dry the milk-coated material. Another way to produce the milky material would be to add milk to a solid polymer which is to be used to form the non-woven component of the pad assembly after the polymer is melted by before it is converted into a fiber form, and then run the polymer-milk mixture through a spinneret so that the milk is incorporated into the polymer fiber.

BRIEF DESCRIPTION OF THE DRAWINGS

This invention will be more readily understood from the following detailed description of a preferred embodiment thereof when taken in conjunction with the accompanying drawings wherein.

DETAILED DESCRIPTION OF THE INVENTION

Figure 1:
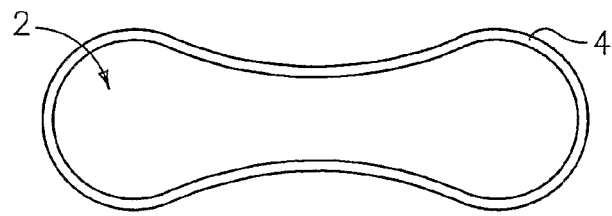
FIG. 1 is a plan view of a first embodiment of a mini pad assembly which is formed in accordance with this invention.
Figure 2:
FIG. 2 is a side elevational view of the mini pad assembly of FIG. 1.
Figure 3:
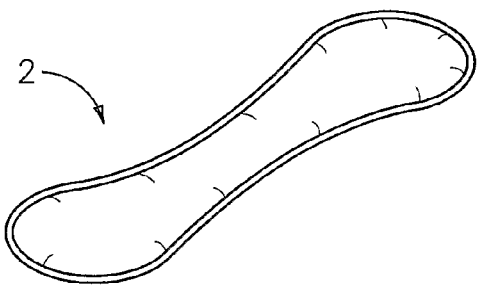
FIG. 3 is perspective view of the mini pad assembly of FIG. 1.
Figure 4:
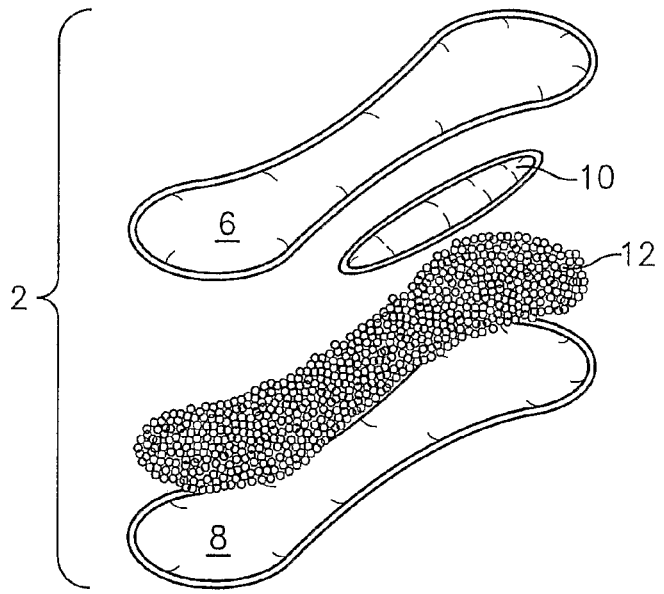
FIG. 4 is an exploded view of the mini pad assembly of FIG. 1.
Figure 4A:
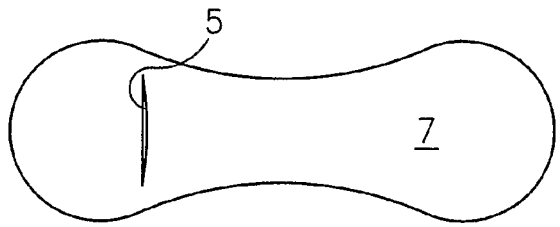
FIG. 4a is a plan view of an outer pouch component which may be used to house the assembly of FIG. 1.
Figure 5:
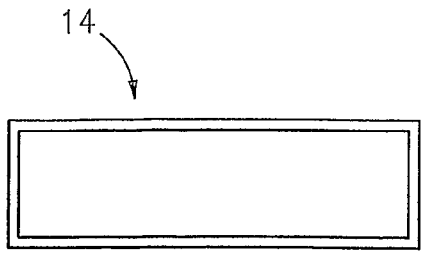
FIG. 5 is a plan view of a core component of a second embodiment of a mini pad assembly which is formed in accordance with this invention.
Figure 6:
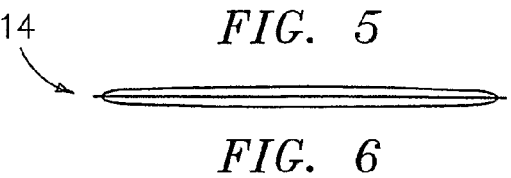
FIG. 6 is a side elevational view of the core component of FIG. 5.
Figure 7:
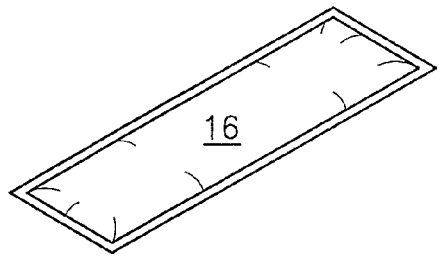
FIG. 7 is perspective view of the core component of FIG. 5.
Figure 8:
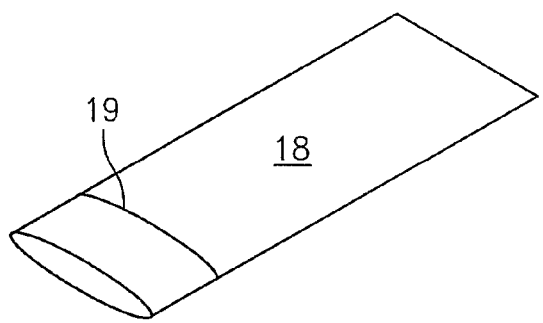
FIG. 8 is a perspective view of a sleeve component of the second embodiment of a mini pad assembly.

Referring now to the drawings, there is shown in FIGS. 1-4a, a first embodiment of a mini pad assembly which is formed in accordance with this invention, and which is designated generally by the numeral 2. This mini pad assembly 2 is a disposable assembly which requires refrigeration prior to use. The mini pad assembly 2 has outer components 6 and 8 which are formed from a non-woven sheet material that is impregnated with nonfat dry milk. The sheets 6 and 8 deliver the milk constituent of the pad assembly 2 to the vulvar tissues when the pad assembly 2 is worn. An inner component 10 of the pad assembly 2 contains an endothermic cooling component material that can be refrigerated, to provide the cold required by the pad assembly 2. A further optional inner component 12 is a layer of exothermic beads which may be ammonium nitrate for example. The several components of the pad 2 may be formed as a pouch by sealing or otherwise adhering the edges 4 of the two sheets 6 and 8 together. The assembly 2 can be made reusable by inserting it through a slit 5 into an outer permeable pouch 7 shown in FIG. 4a which will directly contact the vulvar tissues and will allow through passage of the milk to the vulvar tissues. Alternatively, the outer pouch 7 may be impregnated with dry nonfat milk. The pouch 7 will be provided with adhesive strips (not shown) to facilitate securement of the assembly to the wearer's undergarments. If the pouch 7 is used, after the assembly is used, the inner assembly 2 can be removed from the pouch 7, and the pouch 7 can be discarded. The inner assembly 2 can then be refrigerated again and placed in another pouch for further use.

Figure 9:
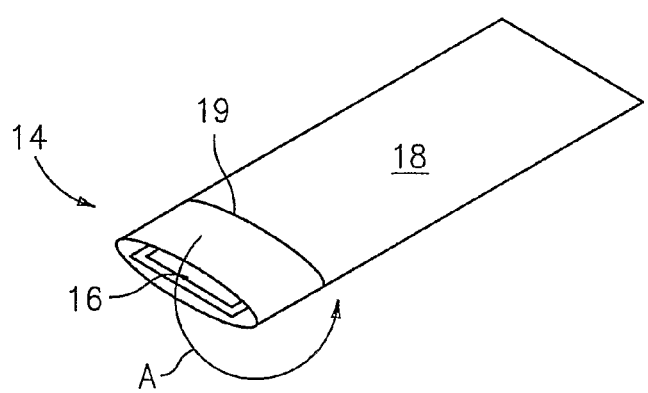
FIG. 9 is a perspective view of the assembled mini pad assembly indicating how the core component is inserted into the sleeve component.

FIGS. 5-9 disclose a second embodiment of the mini pad assembly of this invention which is a single use embodiment that does not require refrigeration. This second embodiment includes a core component 14 in the form of a pouch which contains a crushable endothermic cooling component refrigerant compound which, when squeezed, or crushed, provides the necessary cold for the assembly to operate properly. The crushable cooling component refrigerant can include endothermic reaction compounds of the types described in U.S. Pat. Nos. 4,780,117 Lahey; 4,986,076 Kirk; 6,233,945 Kohout; and 6,393,843 Kohout, the contents of which are incorporated into this application in their entirety. An outer sleeve 18 which is formed from a non woven material is also included. The outer sleeve 18 is coated or impregnated with non fat dry milk. The sleeve 18 has three sealed edges and one open end. The sleeve 18 may also be formed with a fold line 19 which allows the sleeve 18 to be closed after the core 16 is placed in the sleeve 18, as shown in FIG. 9. The open end of the sleeve 18 is simply folded back as indicated by the arrow A and a strip of tape will be used to secure it in place. In the single use version of the mini pad assembly the entire assembly is discarded after use thereof. The sleeve 18 will be provided with adhesive strips (not shown) to facilitate securement of the assembly to the wearer's undergarments.

With both embodiments of the mini pad assembly, when the assembly is worn, the milk impregated component will be disposed against the vulvar tissue. This allows transepidermal moisture to penetrate the milk impregnated component so as to moisten the dried milk in the component. The pad assembly can be brought into contact with the vulvar area of the user in the same manner that conventional mini pads are. It will be readily appreciated that the mini pad assembly of this invention provides a simple, reliable and convenient treatment whereby vulvar irritation can be relieved. The pad assembly can be worn during most common daily activities and is not restricted to in-house usage. The pad assembly is not messy to use, and extended use of it will not result in any adverse effects to the user.

Since many changes and variations of the disclosed embodiments of the invention may be made without departing from the inventive concept, it is not intended to limit the invention otherwise than as required by the appended claims.

What is claimed is:

1. A method for reducing vulvar inflammation and lowering acidity of a female's vulva which acidity results from vaginal secretions which are present in vulvar tissue, said method comprising the step of applying a combination of cold and skim milk to the inflamed tissue.

* * * * *